United States Patent
Barnard et al.

(10) Patent No.: US 8,206,307 B2
(45) Date of Patent: Jun. 26, 2012

(54) ULTRASOUND IMAGING PROBE AND METHOD

(75) Inventors: William Barnard, Maple Valley, WA (US); David Bartholomew Shine, Littleton, CO (US)

(73) Assignee: dBMEDx Inc., Littleton, CO (US)

( * ) Notice: Subject to any disclaimer, the term of this patent is extended or adjusted under 35 U.S.C. 154(b) by 99 days.

(21) Appl. No.: 12/948,622

(22) Filed: Nov. 17, 2010

(65) Prior Publication Data

US 2011/0224551 A1    Sep. 15, 2011

Related U.S. Application Data

(60) Provisional application No. 61/312,363, filed on Mar. 10, 2010.

(51) Int. Cl.
*A61B 8/14*     (2006.01)
(52) U.S. Cl. ........ 600/459; 600/445; 600/443; 600/444; 600/437
(58) Field of Classification Search .................. 600/437, 600/443, 444, 445, 459
See application file for complete search history.

(56) References Cited

U.S. PATENT DOCUMENTS

| | | | |
|---|---|---|---|
| 4,567,895 A | 2/1986 | Putzke | 128/660 |
| 4,926,871 A | 5/1990 | Ganguly et al. | 128/660.07 |
| 5,070,879 A | 12/1991 | Herres | 128/660.08 |
| 5,699,805 A | 12/1997 | Seward et al. | 128/662.06 |
| 6,036,646 A | 3/2000 | Barthe et al. | 600/459 |
| 6,213,948 B1 | 4/2001 | Barthe et al. | 600/445 |
| 6,689,066 B1 | 2/2004 | Omura et al. | 600/463 |
| 2008/0312536 A1 | 12/2008 | Dala-Krishna | 600/459 |

*Primary Examiner* — Brian Casler
*Assistant Examiner* — Joel Lamprecht
(74) *Attorney, Agent, or Firm* — Seed IP Law Group PLLC (57) ABSTRACT

An ultrasound probe is provided having an ultrasound module received in a housing thereof, the ultrasound module including a plurality of transducers longitudinally spaced apart within the housing and a control and processing system electrically coupled to the transducers for collecting ultrasonic data representative of a target biological tissue when the ultrasound probe is in operation. A motor is likewise received in the housing to rotate, oscillate and/or translate the ultrasound module in a data collection mode. Coupling fluid is received in the housing to at least partially surround the ultrasound module and the motor. A method of obtaining ultrasonic data representative of a target biological tissue, such as a bladder, for diagnostic purposes is also provided.

35 Claims, 7 Drawing Sheets

ULTRASOUND IMAGING PROBE AND METHOD

CROSS-REFERENCE TO RELATED APPLICATION

This application claims the benefit under 35 U.S.C. §119(e) of U.S. Provisional Patent Application No. 61/312,363 filed Mar. 10, 2010, incorporated herein by reference in its entirety.

BACKGROUND

1. Technical Field

This disclosure generally relates to ultrasound probes, and more particularly to ultrasound probes having volume scanning capabilities and methods of using ultrasound probes for diagnostic purposes, such as, for example, determining bladder volume.

2. Description of the Related Art

Traditional three-dimensional (C-mode) ultrasound has been accomplished by sweeping a single scanline through target tissue with some combination of mechanical and electronic beam formation. For example, one method is to use a two-axis mechanical stepper motor configuration to move a single piston transducer. Other approaches have been to use electronic B-mode scanheads and add a single motor or a human operator to address the third dimension. Still another approach is to use a full up three dimensional electronically steered phased-array transducer.

Since ultrasound is a pulse-echo technology, the frame rate is limited by the transit time of the pulse-echo cycle. This constraint on frame rate can become overly restrictive as desired resolution increases and even more so when moving from two dimensional (B-mode) to three dimensional (C-mode) imaging. Reduced frame rates increase the likelihood of image blurring from operator movement, patient movement or patient anatomical movement, such as, for example, blood flow or respiration.

For certain diagnostic methods, such as, for example, bladder volume measurements, a single piston transducer swept through spherical coordinates with a multi-angular stepper motor has been used for years. While reasonably inexpensive to manufacture, this topology suffers from several deficiencies that compromise the accuracy of obtained data. For example, with respect to bladder volume measurements, the volumetric resolution of the system typically decreases in both angular directions with depth. Further, bladders that are closer to the patient's skin surface have a much smaller probability of fitting within the total scan solid angle of the system. This is because the bladder is anatomically located beneath the pubic bone where smaller scan cone angles of the system (which are typically less than 90 degrees) are unable to reach. Still further, the center of the cone has redundant scan lines which create processing inefficiencies and increase the maximum ultrasound exposed tissue which may decrease safety to some extent. Further, with systems that utilize a two-axis mechanical stepper topology, the result is one of the slowest frame rates available which increases image blurring and hence measurement accuracy. The combined effect of these deficiencies is an increased reliance on operator training and proper aiming of ultrasound imaging devices.

Consequently, Applicant believes improved diagnostic ultrasound imaging probes and methods are desirable. The ultrasound probes should be easier to aim and use to obtain accurate imaging results for diagnostic purposes. The ultrasound probes should also have a small, robust form factor or package.

BRIEF SUMMARY

The diagnostic ultrasound imaging probes and methods described herein provide for the efficient and accurate collection of three dimensional data representative of a target biological sample in a particularly small, robust form factor. In various embodiments, the ultrasound imaging probes and methods are well adapted for automatically determining the volume of a human bladder irrespective of operator skill in aiming or manipulating the ultrasound probe.

At least one embodiment of an ultrasound probe adapted for efficiently and accurately obtaining three dimensional data of a target biological sample may be summarized as including a housing having a longitudinal axis; an ultrasound module received in the housing, the ultrasound module having a plurality of transducers longitudinally spaced apart within the housing and a control and processing system communicatively coupled to the transducers and operable to cause the transducers to emit ultrasound waves and to process ultrasound signals received via the transducers to collect ultrasonic data representative of a target biological tissue when the ultrasound probe is in operation; a motor received in the housing and drivingly coupled to rotate the ultrasound module about the longitudinal axis of the housing; and a coupling fluid received in the housing to at least partially surround the ultrasound module and the motor. The motor may be a DC motor driven to continuously rotate the ultrasound module about the longitudinal axis of the housing. The motor may be a stepper motor driven to sweep the ultrasound module back and forth about the longitudinal axis of the housing. The coupling fluid may be a non-corrosive, bio-compatible fluid. The housing may be cylindrical. The housing may be an optically and acoustically transparent thermoplastic elastomer. A surface of the housing may include a curvilinear profile such that scan lines of the transducers are redirected when passing through the housing. The curvilinear profile of the surface of the housing may include a periodic sequence of generally symmetric profile segments, a pitch of the segments equal to a pitch of the transducers. The ultrasound module and motor may be hermetically sealed in a common chamber of the housing. The control and processing system may include a wireless communication device to transmit the ultrasonic data representative of the target biological tissue to a remote device. The control and processing system may include a sensor to measure at least one of a rotational position or a rotational speed of the ultrasonic module.

The ultrasound probe may further include a battery, the battery, a base of the motor and the ultrasound module rigidly coupled together to rotate or pivot about the longitudinal axis in unison. The motor may be a dual motion linear and rotary actuator, the dual motion linear and rotary actuator drivingly coupled to the housing to move the ultrasound module relative to the housing linearly along the longitudinal axis and rotationally about the longitudinal axis, either simultaneously or independently. The battery, the base of the motor and the ultrasound module may rotate and translate in unison within a common chamber of the housing filled with coupling fluid.

The ultrasound probe may further include a slip ring coupled to the motor to provide power to the control and processing system of the ultrasound module as the ultrasound module rotates about the longitudinal axis of the housing.

The ultrasound probe may further include a number of flexible electrical conductors electrically coupled to the motor to transmit power to the control and processing system of the ultrasound module as the ultrasound module sweeps back and forth about the longitudinal axis of the housing, the flexible electrical conductors winding and unwinding about the longitudinal axis as the ultrasound module sweeps back and forth.

The ultrasound probe may further include a plurality of LEDs communicatively coupled to the control and processing system to controllably illuminate as the ultrasound module rotates about the longitudinal axis to visually communicate information to a user through the housing.

The ultrasound probe may further include a support structure, the transducers pivotably coupled to the support structure to tilt in parallel about a respective tilt axis perpendicular to the longitudinal axis of the housing. The ultrasound probe may further include a shaft received in the support structure and coupled to the transducers to tilt the transducers about a respective tilt axis perpendicular to the longitudinal axis of the housing as the shaft is translated along the longitudinal axis of the housing.

The ultrasound probe may further include a screw-type shaft coupled to the electric motor to simultaneously rotate and translate the ultrasound module about and along the longitudinal axis, respectively.

An ultrasound probe may be summarized as including a housing having a longitudinal axis; an ultrasound module, the ultrasound module having a plurality of transducers longitudinally spaced apart within the housing and a control and processing system communicatively coupled to the transducers and operable to cause the transducers to emit ultrasound waves and to process ultrasound signals received via the transducers to collect ultrasonic data representative of a target biological tissue when the ultrasound probe is in operation; a battery to power the ultrasound module; and a motor having a base and a drive shaft, the drive shaft of the motor drivingly coupled to the housing, either directly or indirectly, to rotate the ultrasound module, the battery and the base of the motor in unison about the longitudinal axis of the housing. The motor may be a dual motion linear and rotary actuator, the dual motion linear and rotary actuator drivingly coupled to the housing to move the ultrasound module relative to the housing linearly along the longitudinal axis and rotationally about the longitudinal axis, either simultaneously or independently.

A method of obtaining ultrasonic data representative of a target biological tissue, such as a bladder, for diagnostic purposes, may be summarized as including moving an ultrasound module contained in a housing about a longitudinal axis, the ultrasound module including a plurality of transducers longitudinally spaced apart within the housing and a control and processing system electrically coupled to the transducers, the transducers and the control and processing system of the ultrasound module sealed in a common fluid chamber; firing the ultrasound transducers to emit ultrasound waves while the ultrasound module moves about the longitudinal axis; and receiving the ultrasonic data representative of the target biological tissue. Receiving the ultrasonic data representative of the target biological tissue may include receiving information indicative of a volume of a bladder. Moving the ultrasound module contained in the housing about the longitudinal axis of the housing may include continuously rotating the ultrasound module around the longitudinal axis. Moving the ultrasound module contained in the housing about the longitudinal axis of the housing may include pivoting the ultrasound module back and forth about the longitudinal axis in opposite rotational directions. Moving the ultrasound module contained in the housing about the longitudinal axis may include moving the ultrasound module, a battery and a base of a motor in unison about the longitudinal axis. Moving the ultrasound module contained in the housing about the longitudinal axis may include rotating and translating the ultrasound module axially about and along the longitudinal axis, respectively. Rotating and translating the ultrasound module axially about and along the longitudinal axis may include translating the ultrasound module along the longitudinal axis beneath a curvilinear profile of the housing.

The method may further include wirelessly transmitting the ultrasonic data representative of the target biological tissue to a device remote from the ultrasound module.

The method may further include selectively illuminating a plurality of LEDs electrically coupled to the ultrasound module as the ultrasound module moves about the longitudinal axis to visually communicate information to a user through the housing.

The method may further include sensing a rotational position of the ultrasound module; and coordinating a collection of ultrasonic data from the transducers with the position of the ultrasound module.

The method may further include tilting the transducers about a respective tilt axis perpendicular to the longitudinal axis of the housing.

The method may further include simultaneously translating the ultrasound module along the longitudinal axis of the housing as the ultrasound module rotates.

The method may further include prior to moving the ultrasound module, independently translating the ultrasound module along the longitudinal axis of the housing.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles may not be drawn to scale, and some of these elements may be arbitrarily enlarged and positioned to improve drawing legibility.

DETAILED DESCRIPTION

In the following description, certain specific details are set forth in order to provide a thorough understanding of various disclosed embodiments. However, one skilled in the relevant art will recognize that embodiments may be practiced without one or more of these specific details. In other instances, well-known structures, manufacturing techniques and diagnostic methods associated with ultrasound probes may not be shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

FIGS. 1 through 4 show an ultrasound imaging probe 10 according one embodiment. The ultrasound imaging probe 10 includes a main housing 12 coupled to a base or grip 14 for positioning the housing 12 proximate a target sample. Alternatively, the housing 12 may not be coupled to a base or grip 14. The housing 12 can be positioned proximate a target sample directly. Positioning devices, such as, for example, fixtures, belts, straps or the like, may also be provided in certain diagnostic applications to assist in locating the probe 10 relative to a target sample.

Figure 1:
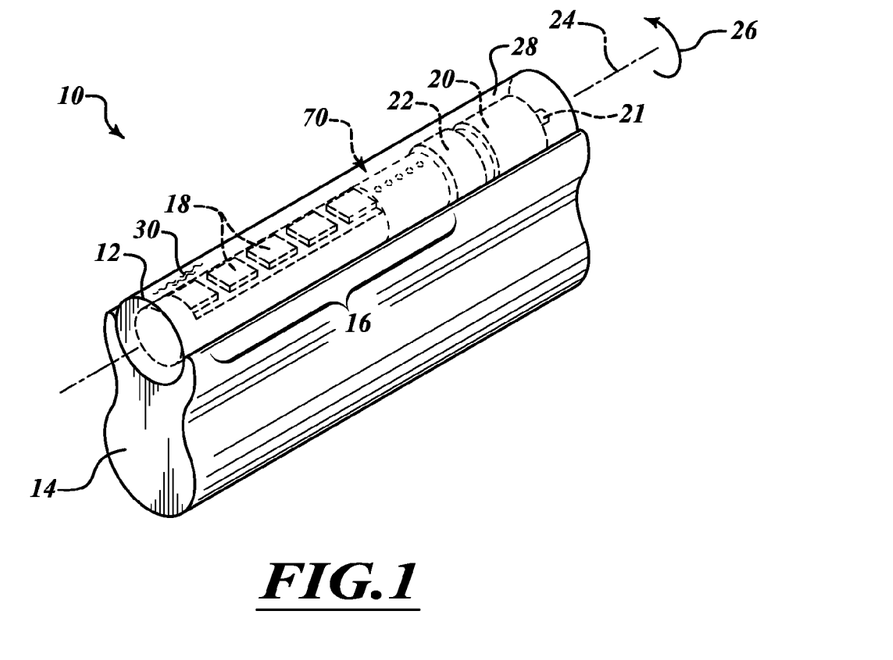
FIG. 1 is an isometric view of an ultrasound probe according to one embodiment.

The ultrasound imaging probe 10 enables a user to quickly and accurately obtain three dimensional data representative of a target sample with minimal skill required in aiming and manipulating the probe 10. The user need only place the probe 10 proximate the target sample and activate the probe 10 to automatically collect data representative of the target sample. The probe 10 may be activated by a switch (not shown), such as a push button switch, on an end or side of the housing 12. As another example, the switch may be a wireless switch, such as, for example, a hall effect switch, so as to allow activation of the ultrasound probe without the need for electrical connections or components of the switch to penetrate an inner chamber of the housing 12.

According to the illustrated embodiment of FIG. 1, the housing 12 of the probe 10 contains an ultrasound module 16 including a plurality of transducers 18, a motor 20 and a power source in the form of a battery 22. The motor 20 is mechanically and electrically coupled to the ultrasound module 16 to rotate or oscillate the ultrasound module 16 about a longitudinal axis 24 of the housing 12 in the direction indicated by the arrow labeled 26, for example. This can be accomplished, for example, by the motor 20 rotating or pivoting a drive shaft 21 thereof that is fixedly coupled to the housing 20 either directly or indirectly. The motor 20 may be a DC motor controllable to rotate the ultrasound module 16 continuously about the longitudinal axis 24 when in a data collection mode. In such embodiments, since the transducers 18 are swept a full, continuous 360 degree rotation, the B-mode images are maximally wide, thus relieving the need for skilled aiming of the probe 10. In other embodiments, the motor 20 may be a stepper motor controllable to sweep the ultrasound module 16 back and forth (i.e., oscillate) about the longitudinal axis 24. Embodiments featuring a back and forth oscillating or pivoting motion may achieve suitable speed and field of view, but may not be as fast or provide as much field of view as embodiments that rotate the ultrasound module 16. Irrespective of rotational capabilities, the ultrasound module 16, motor 20 and battery 22 are contained within a common internal chamber 28 of the housing 12 and surrounded with an ultrasound coupling fluid 30. The coupling fluid 30 is preferably a non-corrosive, bio-compatible fluid, such as, for example, mineral oil.

The housing 12 may be cylindrical or some other suitable shape. The cylindrical shape presents a consistent ultrasound path with some inherent advantageous focusing. In addition, the cylindrical shape is easy to manufacture, is mechanically robust and provides a convenient vessel in which to seal in the coupling fluid 30. The cylindrical shape may also limit the number of edges, which might otherwise present a source of discomfort or even injury to a patient or medical care provider. The housing 12 is made of a material that is acoustically transparent and in some embodiments optically transparent or translucent. For example, the housing 12 may be an acoustically and optically transparent thermoplastic elastomer, such as, for example, a material available from Arkema Inc. under the name PEBAX®. Alternatively, the housing 12 may be acrylic or another plastic material.

Figure 2:
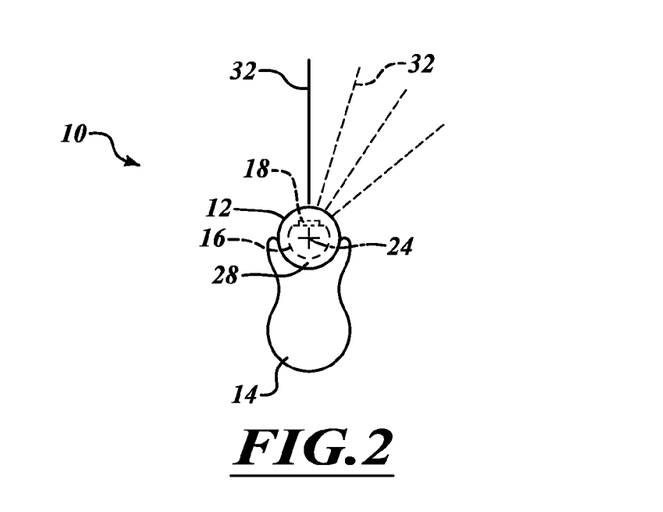
FIG. 2 is a side elevation view of the ultrasound probe of FIG. 1.
Figure 3:
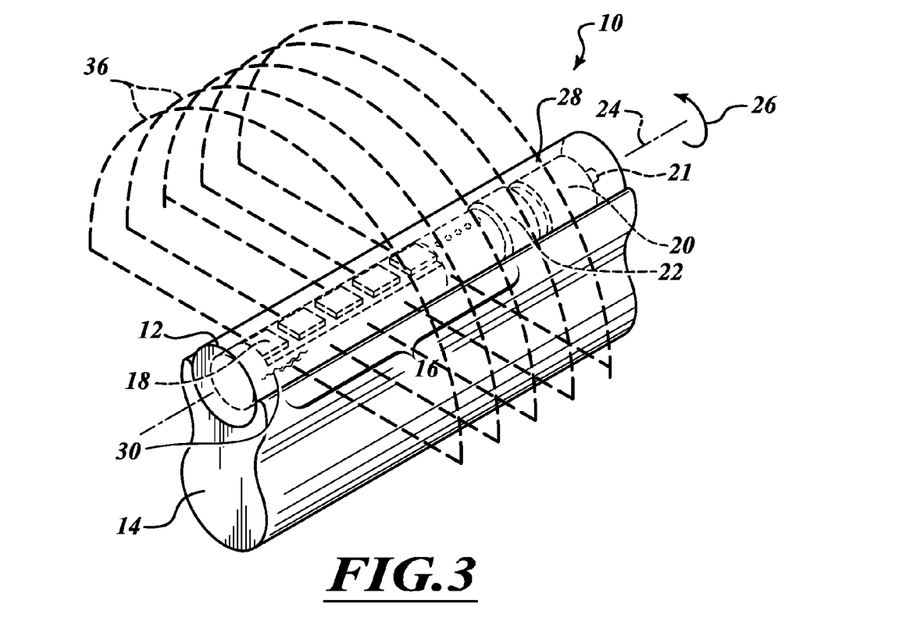
FIG. 3 is an isometric view of the ultrasound probe of FIG. 1 illustrating scan planes.
Figure 4:
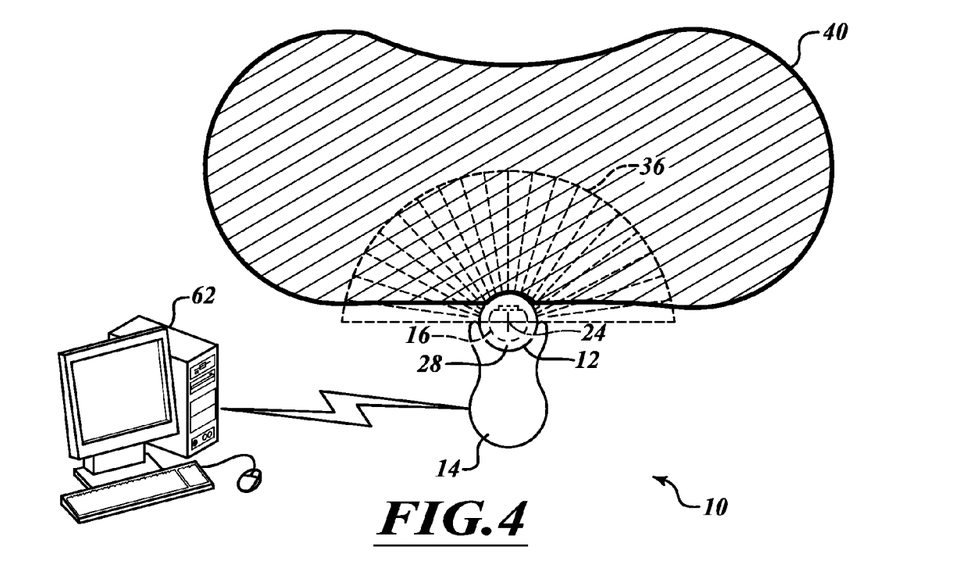
FIG. 4 is a side elevation view of the ultrasound probe of FIG. 1 illustrating a scan plane sweeping through a target sample.

FIG. 2 shows an end view of the ultrasound probe 10 and illustrates sequential A-mode scan lines 32 radiating from the transducers 18. These A-mode scan lines 32 are combined to form B-mode images as the transducers 18 rotate as represented by the scan planes 36 shown in FIG. 3. FIG. 4 shows the ultrasound probe 10 proximate a target biological sample 40 with a scan plane 36 of the transducers 18 sweeping through the target biological sample 40 as the transducers 18 rotate within the housing 12.

Although the illustrated embodiment shows five transducers (i.e., ultrasound transducers) 18 of generally rectangular shape, it is appreciated that more or fewer transducers 18 may be provided and that the transducers 18 may vary in shape and size. In addition, the transducers 18 may be spaced regularly or irregularly along a length of the ultrasound module 16. Still further, the transducers 18 may vary in frequency and focusing capability.

For example, the ultrasound module 16 may include eight 3.7 Mhz transducers 18 equally spaced along a length of the ultrasound module 16, for instance, at about 10 mm apart, to form eight parallel B-mode slices that combine to create a C-mode image that ensonifies a sector volume. The transducers 18 may have a rectangular profile of about 11 mm×8 mm which provide excellent 25λ (3.7 MHz) focusing in a phi axis of rotation and reasonable 18λ (3.7 Mhz) focusing in the z axis between scan planes. Slightly less focusing may be designed into the z axis since the least amount of spatial resolution exists between scan planes. It is noted that a 3.7 Mhz frequency gives excellent axial resolution into an abdomen and is conveniently chosen as an integer multiple of the standard universal asynchronous receiver/transmitter (uart) clock rate 3.68 Mhz. Values from 1-7 MHz, however, are also sufficient for bladder imaging and similar applications.

Advantageously, in various embodiments the sweep of the B-mode image generated by a corresponding transducer 18 can be varied by gating the number of A-mode scan lines that are collected. For example, in embodiments featuring continuous rotation of the ultrasound module 16, the transducers 18 of the ultrasound module 16 may be activated throughout 360 degrees of rotation, or over a portion of the same, to collect three dimensional data over varying ranges. In an example, the transducers 18 are active over about 180 degrees of rotation to create a hemicylindrical scan volume, as illustrated in FIGS. 3 and 4. Similarly, when oscillated or swept back and forth, the transducers 18 may be swept through various angle ranges, such as, for example, 120, 150, and 180 degrees or more.

Figure 5:
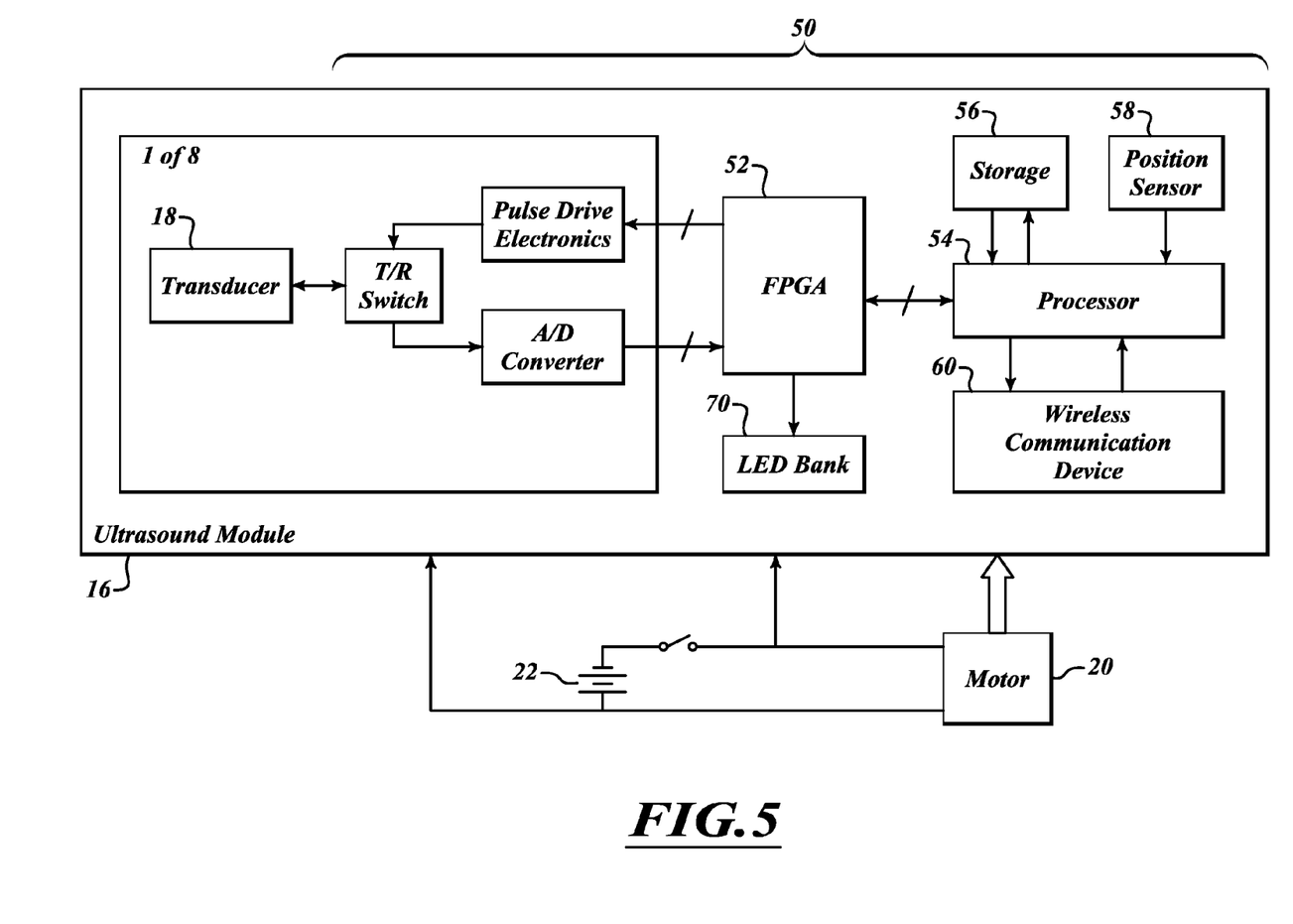
FIG. 5 is a block diagram illustrating an example ultrasound module rotatably coupled to a motor and powered by a battery.

FIG. 5 shows an ultrasound module 16 which is rotated within the housing 12 of the ultrasound probe 10 by a motor 20 and powered by a battery 22 according to one illustrated embodiment. In particular, the illustrated example of FIG. 5 includes a control and processing system 50 with various electrical components that enable functionality of the ultrasound probe 10. For example, one or more application specific integrated circuits (ASICs) programmable gate or arrays (PGAs) 52 may be coupled to a microprocessor 54 for controlling and coordinating the various functions of the ultrasound probe 10, including rotation of the ultrasound module 16 and transmitting and receiving of high frequency sound waves from each of the transducers 18. The control and processing system 50 may include discrete analog to digital converters (ADCs) and/or discrete digital to analog converters (DACs). Alternatively, the ADC and/or DAC functions may be implemented in the ASIC or PGA. The control and processing system 50 may further include power supply circuitry, for example an inverter, rectifier, step up or step down converter, transformer, etc. The control and processing system 50 may further include transmit and timing control circuitry to control waveform timing, aperture and focusing of the ultrasound pressure waves.

The control and processing system 50 further includes a storage device 56 (e.g., serial flash), a rotational position sensor 58 (e.g., hall-effect sensor, optical encoder) and a wireless communication device 60 (e.g., Bluetooth radio module or other suitable short-range wireless device). The storage device 56 enables temporary storage of data, control signals, instructions and the like. The position sensor 58 enables the control and processing system 50 to coordinate the transmitting and receiving of high frequency sound waves from each of the transducers 18 with the rotational position of the ultrasound module 16. The wireless communication device 60 enables data output from the ultrasound module 16 to remote devices for further processing or evaluation, such as, for example, a remote evaluation device 62 (FIG. 4) having components such as a monitor or other display devices, a keyboard, a printer and/or other input and output devices. In this manner, diagnostic data may be collected with the probe 10 in a particularly small form factor of package, such that the user may obtain such data with minimal bother or inconvenience to the host of the target sample and without interference from otherwise bulky components or cables. Of course, in some embodiments an extensive user interface, including for example a display, keypad, printer and/or other input and output devices may be integrated with the probe 10 for further evaluation or processing onboard.

By containing the entire analog and digital processing circuitry of the control and processing system 50 in a small form factor which can be spun by the motor 20, the number of electrical connections which are maintained across a static/dynamic (rotational or oscillating) interface can be minimized or even eliminated. For example, the motor 20, the power source (e.g., battery 22) and the ultrasound module 16 (including the control and processing system 50) may be rigidly coupled together to rotate or pivot about the longitudinal axis 24 in unison. Also for example, the motor 20 may be a dual motion linear and rotary actuator drivingly coupled to the housing 12 to move the ultrasound module 16 (and hence control and processing system 50) relative to the housing 12 both linearly along the longitudinal axis 24 and rotationally about the longitudinal axis 24, either simultaneously or independently. In this manner, the battery 22, motor 20 and ultrasound module 16 may rotate and/or translate in unison within a common chamber 28 of the housing 12 such that all electrical connections for enabling the functionality of the probe 10 remain static relative to each other. Alternatively, the motor 20 and battery 22 may remain fixed relative to the housing 12 and drivingly rotate and/or translate the ultrasound module 16. In such embodiments, particularly those featuring continuous rotation of the ultrasound module 16, a slip ring or similar device may be coupled to the motor 20 to transmit electrical power to the control and processing system 50 of the ultrasound module 16 as the ultrasound module 16 rotates about the longitudinal axis 24 of the housing 12. In those embodiments featuring an oscillating, pivoting or back and forth sweeping motion of the ultrasound module 16, a slip ring or similar device may likewise be provided. In some instances, the number of slip ring connections may be reduced to only power and ground such that the entire ultrasound module 16 is relatively immune from conducted noise sources. Since only power and ground are provided, the slip ring does not need to be exceptionally electrically quiet and even a ball bearing race can be sufficient to transmit power as well as provide a nice stable mechanism for rotatably supported the ultrasound module 16. In these embodiments, the electrical connections between the power source (e.g., battery 22), motor 20 and ultrasound module 16 may be through wires, wiping blades, ball-bearing connections, concentric sleeves or other direct connections. Alternatively, power may be provided to the ultrasound module 16 inductively, thereby eliminating all direct electrical connections at the static/dynamic (i.e., rotational or oscillating) interface that may be present between the motor 20 and ultrasound module 16.

In some embodiments in which the motor 20 and power source 22 do not rotate with the ultrasound module 16, wires or a flex circuit may be directly connected to the control and processing system 50 to wind and unwind about the rotational axis as the ultrasound module 16 and hence control and processing system 50 rotate relative to the other components. In these embodiments in particular, the housing 12 may include a data transfer port, such as a USB port, in addition to or in lieu of the wireless communication device 60. However, providing such a port is mechanically more complicated and increases susceptibility of the ultrasound probe 10 to static interference and conducted noise interference from the additional connections.

The control and processing system 50 may further include or be communicatively coupled to an LED bank 70 to create a display viewable to a user through a surface of the housing 12. For example, an LED bank 70 in the form of a linear arrangement of individual LEDs may be provided to rotate with the ultrasound module 16 to create a multi-character display that is visible as the LEDs rotate. In this arrangement, two dimensional characters can be formed via the LEDs by controllably illuminating the LEDs to create a transverse dimension of the characters as the module 16 rotates or pivots. In other words, the control and processing system 50 controls which LEDs are lit as the LED bank 70 rotates such that a given character or series of characters are projected in a readable form. In this manner, error codes, instructional codes, diagnostic test results or other information may be communicated to a user before, during or after use of the ultrasound probe 10. The control and processing system 50 may automatically evaluate collected ultrasonic data and generate diagnostic information, such as, for example, the volume of the target biological sample. This diagnostic information may be displayed directly to a user through the housing 12. In some embodiments, a larger array of LEDs or other display devices may be coupled to the rotating module 16. Alternatively, a display (e.g., LCD, LED, OLED) may be integrated into the static housing 12, although additional electrical connections would then be required through the static/dynamic interface.

Figure 6:
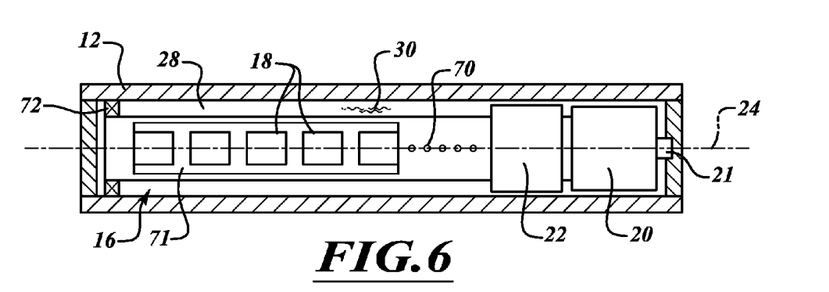
FIG. 6 is a front elevation view of a housing and internal components of the ultrasound probe of FIG. 1.
Figure 7:
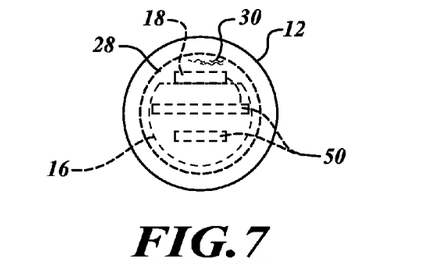
FIG. 7 is a side elevation view of the housing and internal components of FIG. 6.
Figure 8:
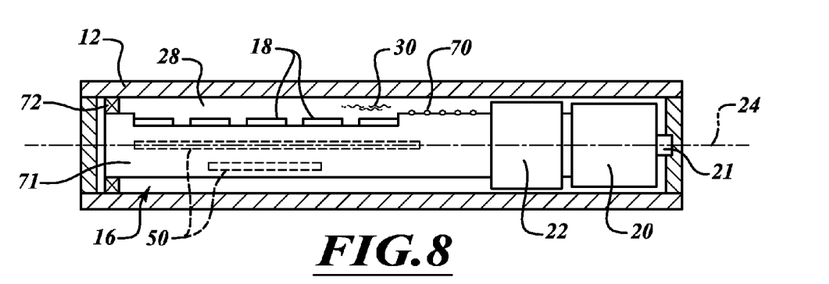
FIG. 8 is a bottom plan view of the housing and internal components of FIG. 6.

As depicted in FIGS. 6 through 8, the various components described above may be received within a common chamber 28 of the housing 12 of the ultrasound probe 10 that is filled with a coupling fluid 30. The coupling fluid 30 advantageously provides lubrication to moving components, a heat sink for electronic components and also ultrasonic coupling between the transducers 18, housing 12 and ultimately the target biological sample 40. As previously described, the coupling fluid 30 may be mineral oil or an equivalent non-corrosive, bio-compatible, ultrasonic coupling fluid.

With continued reference to FIGS. 6 through 8, the ultrasound module 16 is shown longitudinally adjacent the motor 20 and battery 22. As previously described, the battery 22 supplies power to the motor 20 to rotate the entire ultrasound module 16, battery 22 and motor 20 combination about the longitudinal axis of rotation 24 during operation, according to the illustrated embodiment. The ultrasound module 16 includes longitudinally spaced transducers 18 electrically and mechanically coupled to the control and processing system 50. The control and processing system 50 enables collection and subsequent transmission of ultrasonic data indicative of a three dimensional representation of a target sample within the confines of the rotating ultrasound module 16 itself.

The ultrasound module 16 may be attached to a frame 71 which in turn supports the various electrical components of the control and processing system 50, including one or more integrated circuit boards thereof. The frame 71 may be rotatably supported by bearings or guides 72 to maintain the ultrasound module 16 centered within the housing 12 throughout rotational or pivotal movement of the ultrasound module 16. The frame 71 may also support or be rigidly coupled to the battery 22, and a base of the motor 22 such that the ultrasound module 16, battery 22 and motor 20 rotate or pivot in unison during operation. In this manner, as previously described, all functional components and electrical connections between these components remain static relative to each other. Consequently, no electrical connections are required to be maintained across a static/dynamic interface. This is particularly advantageous in that the integrity of the chamber 28 containing the components can remain intact. In addition, mechanisms for transmitting electrical signals or power across a static/dynamic interface can be eliminated. Details of the frame 71 and connections to specific components have not been shown or described in detail to avoid unnecessarily obscuring descriptions of the embodiments.

Alternatively, a base of the motor 20 and the battery 22 may be held static with respect to the housing 12 to drivingly rotate or pivot the ultrasound module 16 with respect thereto. In such embodiments, the ultrasound module 16 may be coupled to the motor 20 via a slip ring or similar connection such that the battery 22 is able to supply power to the control and processing system 50 via the static/dynamic interface of the motor 20 and ultrasound module 16. In one embodiment, electrical connections maintained through the dynamic interface of the motor 20 and ultrasound modules 16 are limited to power and ground. In this manner, the entire ultrasound module 16 is relatively immune from conducted noise sources.

Figure 9:
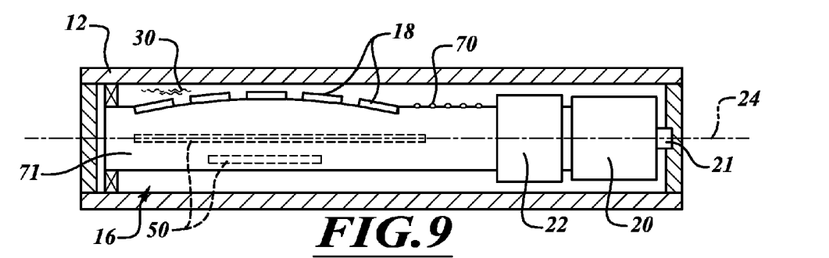
FIG. 9 is a bottom plan view of a housing and internal components according to another embodiment.
Figure 10:
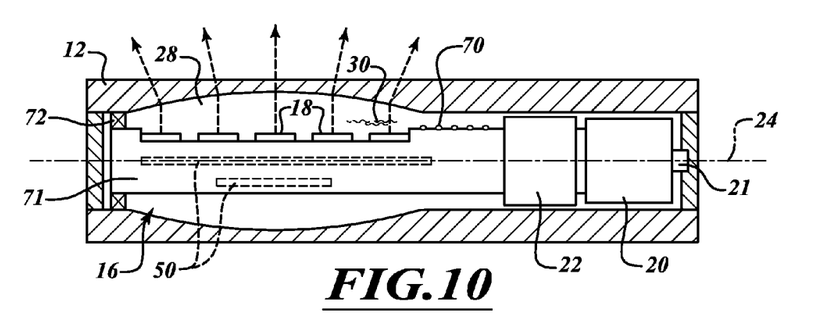
FIG. 10 is a bottom plan view of a housing and internal components according to yet another embodiment.

Although the transducers 18 may be located on the ultrasound module 16 in a common plane, it is appreciated that the orientation and placement of the transducers 18 within the housing 12 may vary. For example, as illustrated in FIG. 9, the transducers 18 may be arranged on a convex surface and splayed outwardly to adjust the scanning profile of the ultrasound probe 10. In addition, as illustrated in FIG. 10, it is appreciated that a profile of the housing 12 may be varied to redirect, steer and/or focus the scanning profile of the ultrasound probe 10. Alternatively, the transducers 18 may be focused or steered electronically without modifications to the profile of the housing 12.

Figure 11A:
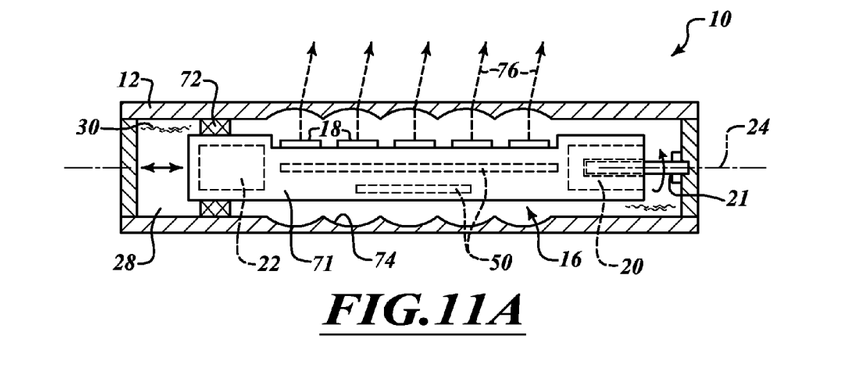
FIG. 11A is a front elevation view of a housing and internal components of an ultrasound probe in a first position, according to another embodiment.
Figure 11B:
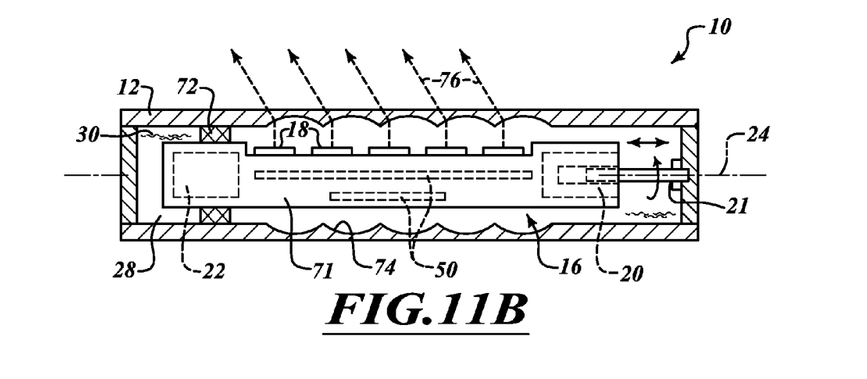
FIG. 11B is a front elevation view of the housing and internal components of the ultrasound probe of FIG. 11A in a second position.

FIGS. 11A and 11B illustrate an ultrasound probe 10 which advantageously enables both lateral and rotational movement of the ultrasound module 16 relative to the housing 12 in a particularly small form factor or package. The transducers 18, control and processing system 50, battery 22 and motor 20 are rigidly coupled together to move in unison during operation via a frame 71 or similar structure. The motor 20 may be a dual motion linear and rotary actuator, the dual motion linear and rotary actuator drivingly coupled to the transducers 18 and other components to move the transducers 18 relative to the housing 12 via a drive shaft 21. The motor 20 may drive the transducers 18 linearly along the longitudinal axis and rotationally about the longitudinal axis, either simultaneously or independently. Consequently, the transducers 18 may advantageously collect additional three dimensional data in an efficient manner. Alternatively, a secondary motor (not shown) may be provided to control translational movement, while the primary motor controls rotational or pivotal movement. The motors may be sequenced or linked to operate simultaneously or the motors may operate independently.

The profile of the housing 12 may be varied to include a curvilinear profile to further enhance the scanning profile of the transducers 18. For example, an interior surface 74 of the housing 12 may include regularly spaced undulations with a pitch corresponding to a pitch of the transducers 18. The profile of the undulations can be shaped for example to redirect scan lines from each of the transducers 18 as they radiate from the housing 12. For example, a central profile of the undulations may be shaped such that a direction of the scan lines is substantially unaffected when the transducers 18 are aligned therewith, while opposing side portions of the undulations may direct the scan lines to varying degrees, such as, for example, up to 45 degrees or more from an axis perpendicular to the longitudinal axis 24. As such, the housing 12 may effectively tilt or sweep the scan lines radiating from the transducers 18 fore and aft as the transducers 18 translate along the longitudinal axis 24, as indicated by the arrows labeled 76. In this manner, the probe 10 is able to advantageously collect three dimensional data of a target biological sample in a particularly efficient and consistent manner. For example, in one embodiment, the probe 10 is able to collect sufficient three dimensional data of a target bladder to calculate a volume of the same with acceptable accuracy via a low duty cycle scanning sequence that may last, for example, in the range of about 5 seconds. This capability allows the probe 10 to make repeated measurements on a single charge of the battery 22. It also allows a user to obtain diagnostic information with minimal bother or inconvenience to the host of the target sample. The battery 22 and hence probe 10 can be recharged inductively by placing the probe 10 in a base charger (not shown) for subsequent and repeated use.

Figure 12:
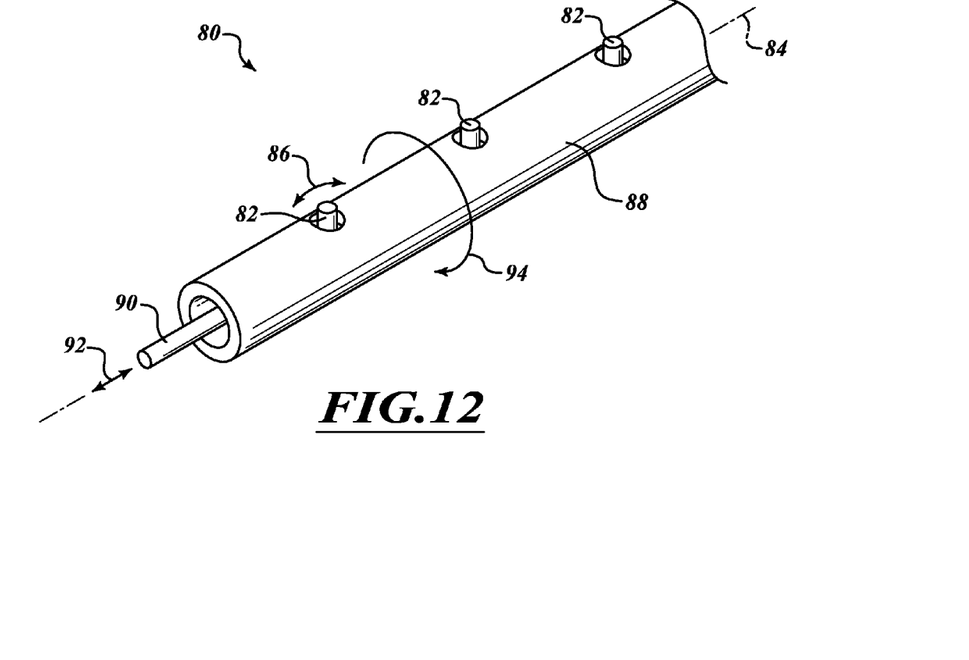
FIG. 12 is a partial isometric view of an ultrasound module according to another embodiment.
Figure 13:
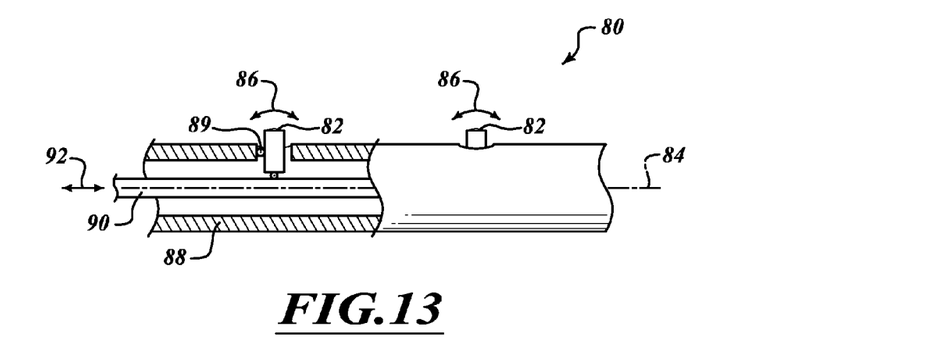
FIG. 13 is a partial front elevation view of the ultrasound module of FIG. 12.

Additionally, although the transducers 18 may be rigidly attached to the ultrasound module 16, it is appreciated that in some embodiments the transducers 18 may be movably coupled to the ultrasound module 16. For example, as illustrated in FIGS. 12 and 13, an embodiment of an ultrasound module 80 may include transducers 82 operable to tilt fore and aft while the ultrasound module 80 rotates about a longitudinal axis 84 as indicated by the arrow labeled 86. According to the illustrated embodiment, the ultrasound module 80 may include transducers 82 that are each pivotably coupled to a cylindrical support structure 88 about a respective tilt axis 89 oriented perpendicular to the longitudinal axis 84 of the ultrasound module 16 and pivotably coupled to a shaft 90 received in the support structure 88. In this manner, the transducers 82 are operable to tilt in parallel toward and away from longitudinal ends of the ultrasound module 80 by pivoting or oscillating about the respective tilt axes 89 as the shaft 90 translates back and forth in the direction indicated by the arrow labeled 92. As such, the transducers 82 may be held in one position while a data set is collected and then tilted slightly in parallel with each other while another data set is collected. This process can be repeated multiple times with the transducers 82 tilted to varying degrees to create a complete high resolution three dimensional data set. In some embodiments, the shaft 90 may be translated and hence transducers 82 tilted independent of the rotational motion of the ultrasound module 80. In other embodiments, the shaft 90 may be coupled or linked to the rotation of the ultrasound module 80 such that the shaft is automatically advanced back and forth in a coordinated manner, such as, for example, after each revolution.

Figure 14:
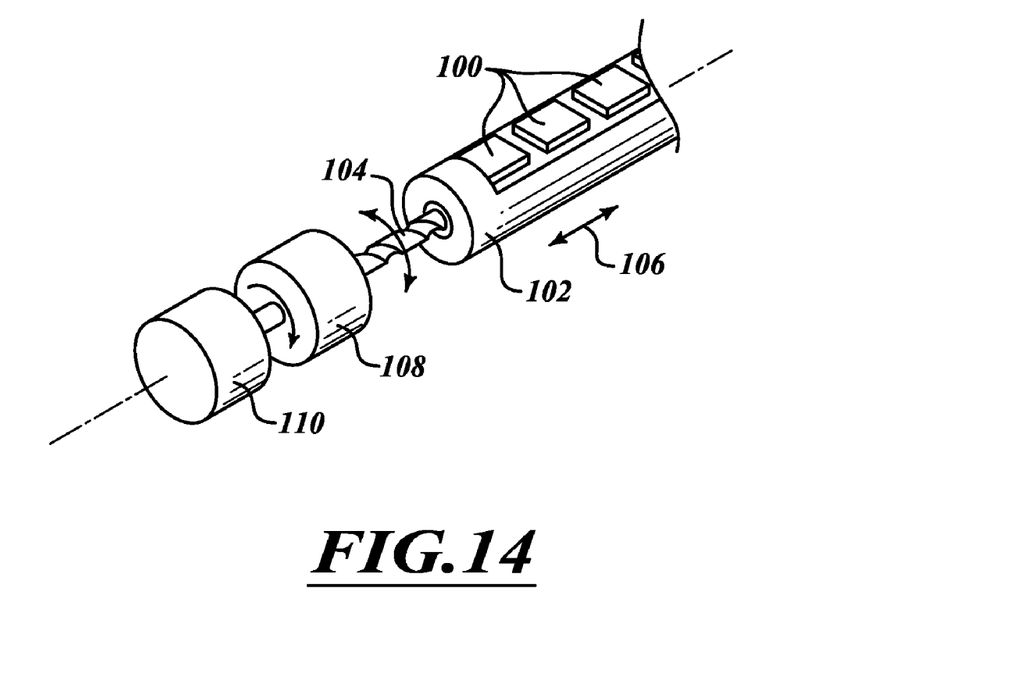
FIG. 14 is a partial isometric view of an ultrasound module and motors according to yet another embodiment.

As another example, transducers 100 may be coupled to a frame or sheath 102 having internal screw-like features that engage a corresponding screw-like rotational shaft 104, as illustrated in FIG. 14. As the shaft 104 rotates in a first direction, the frame or sheath 102 translates the transducers 100 forward. As the shaft 104 rotates in the opposite direction, the frame or sheath 102 draws the transducers 100 back, as indicated by the arrows labeled 106. In such an embodiment, one motor 108 may be used to drive the screw-like shaft 104 to advance and retreat the transducers longitudinally while another motor 110 moves the transducers 100 rotationally. Alternatively, a single motor may be configured or drivingly coupled to perform both rotation and translation of the transducers 100. Wires or a flexible circuit can be attached to electrical components maintained on the frame or sheath 102 to wind and unwind about the rotational shaft 106 as needed; however, in embodiments wherein all functional electrical components rotate or pivot in unison the need for moving wires or a flexible circuit is advantageously eliminated.

Although embodiments of the diagnostic ultrasound imaging probes and methods disclosed herein have been described in connection with ultrasound diagnostic equipment and methods for imaging target biological samples, including bladders in particular, and for determining the volume of the same, it will be apparent to those skilled in the art that these systems, methods and aspects of the same may be applied to other diagnostic imaging applications. Further, it is appreciated that embodiments of the diagnostic ultrasound imaging probes may be designed to be serviceable, such as to enable replacement of the battery or other internal components. A removable housing end cap (not shown) with appropriate seals may be provided for this purpose. Alternatively, the functional components of the probe (i.e., the ultrasound module, motor and power source) may be hermetically and permanently sealed in the housing for disposable use applications.

Moreover, aspects of the various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An ultrasound probe comprising:
 a housing having a longitudinal axis;
 an ultrasound module received in the housing, the ultrasound module having a plurality of transducers longitudinally spaced apart within the housing and a control and processing system communicatively coupled to the transducers and operable to cause the transducers to emit ultrasound waves and to process ultrasound signals received via the transducers to collect ultrasonic data representative of a target biological tissue when the ultrasound probe is in operation;
 a motor received in the housing and drivingly coupled to rotate the ultrasound module about the longitudinal axis of the housing; and
 a coupling fluid received in the housing to at least partially surround the ultrasound module and the motor.

2. The ultrasound probe of claim 1, further comprising:
 a battery, the battery, a base of the motor and the ultrasound module rigidly coupled together to rotate about the longitudinal axis in unison.

3. The ultrasound probe of claim 2 wherein the motor is a dual motion linear and rotary actuator, the dual motion linear and rotary actuator drivingly coupled to the housing to move the ultrasound module relative to the housing linearly along the longitudinal axis and rotationally about the longitudinal axis.

4. The ultrasound probe of claim 3 wherein the battery, the base of the motor and ultrasound module rotate and translate in unison within a common chamber of the housing, the chamber filled with the coupling fluid.

5. The ultrasound probe of claim 1 wherein the motor is a DC motor driven to continuously rotate the ultrasound module about the longitudinal axis of the housing.

6. The ultrasound probe of claim 5, further comprising:
 a slip ring coupled to the motor to provide power to the control and processing system of the ultrasound module as the ultrasound module rotates about the longitudinal axis of the housing.

7. The ultrasound probe of claim 1 wherein the motor is a stepper motor driven to sweep the ultrasound module back and forth about the longitudinal axis of the housing.

8. The ultrasound probe of claim 7, further comprising:
a number of flexible electrical conductors electrically coupled to the motor to transmit power to the control and processing system of the ultrasound module as the ultrasound module sweeps back and forth about the longitudinal axis of the housing, the flexible electrical conductors winding and unwinding about the longitudinal axis as the ultrasound module sweeps back and forth.

9. The ultrasound probe of claim 1 wherein the control and processing system includes a wireless communication device to transmit the ultrasonic data representative of the target biological tissue to a remote device.

10. The ultrasound probe of claim 1 wherein the control and processing system includes a sensor to measure at least one of a rotational position or a rotational speed of the ultrasonic module.

11. The ultrasound probe of claim 1, further comprising:
a plurality of LEDs communicatively coupled to the control and processing system to controllably illuminate as the ultrasound module rotates about the longitudinal axis to visually communicate information to a user through the housing.

12. The ultrasound probe of claim 1, further comprising:
a support structure, the transducers pivotably coupled to the support structure to tilt in parallel about a respective tilt axis perpendicular to the longitudinal axis of the housing.

13. The ultrasound probe of claim 12, further comprising:
a shaft received in the support structure and coupled to the transducers to tilt the transducers about a respective tilt axis perpendicular to the longitudinal axis of the housing as the shaft is translated along the longitudinal axis of the housing.

14. The ultrasound probe of claim 1, further comprising:
a screw-type shaft coupled to the motor to simultaneously rotate and translate the ultrasound module about and along the longitudinal axis, respectively.

15. The ultrasound probe of claim 1 wherein the coupling fluid is a non-corrosive, bio-compatible fluid.

16. The ultrasound probe of claim 1 wherein the housing is cylindrical.

17. The ultrasound probe of claim 1 wherein the housing is an optically and acoustically transparent thermoplastic elastomer.

18. The ultrasound probe of claim 1 wherein the ultrasound module and motor are hermetically sealed in a common chamber of the housing.

19. The ultrasound probe of claim 1 wherein a surface of the housing includes a curvilinear profile such that scan lines of the transducers are redirected when passing through the housing.

20. The ultrasound probe of claim 19 wherein the curvilinear profile of the surface of the housing includes a periodic sequence of generally symmetric profile segments, a pitch of the segments equal to a pitch of the transducers.

21. A method of obtaining ultrasonic data representative of a target biological tissue, such as a bladder, for diagnostic purposes, the method comprising:
moving an ultrasound module contained in a housing about a longitudinal axis, the ultrasound module including a plurality of transducers longitudinally spaced apart within the housing and a control and processing system electrically coupled to the transducers, the transducers and the control and processing system of the ultrasound module sealed in a common fluid chamber;
firing the ultrasound transducers to emit ultrasound waves while the ultrasound module moves about the longitudinal axis; and
receiving the ultrasonic data representative of the target biological tissue.

22. The ultrasound probe of claim 21 wherein moving the ultrasound module contained in the housing about the longitudinal axis includes moving the ultrasound module, a battery and a base of a motor in unison about the longitudinal axis.

23. The ultrasound probe of claim 21 wherein moving the ultrasound module contained in the housing about the longitudinal axis includes rotating and translating the ultrasound module axially about and along the longitudinal axis, respectively.

24. The ultrasound probe of claim 23 rotating and translating the ultrasound module axially about and along the longitudinal axis includes translating the ultrasound module along the longitudinal axis beneath a curvilinear profile of the housing.

25. The method of claim 21 wherein receiving the ultrasonic data representative of the target biological tissue includes receiving information indicative of a volume of a bladder.

26. The method of claim 21 wherein moving the ultrasound module contained in the housing about the longitudinal axis of the housing includes continuously rotating the ultrasound module around the longitudinal axis.

27. The method of claim 21 wherein moving the ultrasound module contained in the housing about the longitudinal axis of the housing includes pivoting the ultrasound module back and forth about the longitudinal axis in opposite rotational directions.

28. The method of claim 21, further comprising:
wirelessly transmitting the ultrasonic data representative of the target biological tissue to a device remote from the ultrasound module.

29. The method of claim 21, further comprising:
selectively illuminating a plurality of LEDs electrically coupled to the ultrasound module as the ultrasound module moves about the longitudinal axis to visually communicate information to a user through the housing.

30. The method of claim 21, further comprising:
sensing a rotational position of the ultrasound module; and
coordinating a collection of ultrasonic data from the transducers with the position of the ultrasound module.

31. The method of claim 21, further comprising:
tilting the transducers about a respective tilt axis perpendicular to the longitudinal axis of the housing.

32. The method of claim 21, further comprising:
simultaneously translating the ultrasound module along the longitudinal axis of the housing as the ultrasound module rotates.

33. The method of claim 21, further comprising:
prior to moving the ultrasound module, independently translating the ultrasound module along the longitudinal axis of the housing.

34. An ultrasound probe comprising:
a housing having a longitudinal axis;
an ultrasound module, the ultrasound module having a plurality of transducers longitudinally spaced apart within the housing and a control and processing system communicatively coupled to the transducers and operable to cause the transducers to emit ultrasound waves and to process ultrasound signals received via the transducers to collect ultrasonic data representative of a target biological tissue when the ultrasound probe is in operation;

a battery to power the ultrasound module; and a motor having a base and a drive shaft, the drive shaft of the motor drivingly coupled to the housing to rotate the ultrasound module, the battery and the base of the motor in unison about the longitudinal axis of the housing.

35. The ultrasound probe of claim 34 wherein the motor is a dual motion linear and rotary actuator, the dual motion linear and rotary actuator drivingly coupled to the housing to move the ultrasound module relative to the housing linearly along the longitudinal axis and rotationally about the longitudinal axis.

* * * * *

UNITED STATES PATENT AND TRADEMARK OFFICE
CERTIFICATE OF CORRECTION

PATENT NO. : 8,206,307 B2  
APPLICATION NO. : 12/948622  
DATED : June 26, 2012  
INVENTOR(S) : William Barnard et al.

Page 1 of 1

It is certified that error appears in the above-identified patent and that said Letters Patent is hereby corrected as shown below:

In the Claims:

Column 14, Line 8:
"22. The ultrasound probe of claim 21 wherein moving the" should read, --22. The method of claim 21 wherein moving the--.

Column 14, Line 12:
"23. The ultrasound probe of claim 21 wherein moving the" should read, --23. The method of claim 21 wherein moving the--.

Column 14, Line 17:
"24. The ultrasound probe of claim 23 rotating and translating" should read, --24. The method of claim 23 wherein rotating and translating--.

Signed and Sealed this
Seventeenth Day of September, 2013

Teresa Stanek Rea
*Deputy Director of the United States Patent and Trademark Office*